United States Patent
Henry et al.

(10) Patent No.: US 9,918,869 B2
(45) Date of Patent: Mar. 20, 2018

(54) CATHETER ASSEMBLY WITH DEPLOYABLE COLLECTION CONTAINER

(71) Applicant: Hollister Incorporated, Libertyville, IL (US)

(72) Inventors: Jerome Anthony Henry, Castlebar (IE); Brendan Joseph Heneghan, Louisburgh (IE); Adam J. Foley, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 375 days.

(21) Appl. No.: 14/775,416

(22) PCT Filed: Mar. 14, 2013

(86) PCT No.: PCT/US2013/031703
§ 371 (c)(1),
(2) Date: Sep. 11, 2015

(87) PCT Pub. No.: WO2014/142923
PCT Pub. Date: Sep. 18, 2014

(65) Prior Publication Data
US 2016/0030226 A1    Feb. 4, 2016

(51) Int. Cl.
*A61F 5/44* (2006.01)
*A61M 25/00* (2006.01)
*A61F 5/451* (2006.01)

(52) U.S. Cl.
CPC ............ *A61F 5/4404* (2013.01); *A61F 5/451* (2013.01); *A61M 25/0017* (2013.01); *A61M 25/002* (2013.01)

(58) Field of Classification Search
CPC ............ A61M 25/0017; A61M 25/002; A61F 5/4404; A61F 5/451
See application file for complete search history.

(56) References Cited

FOREIGN PATENT DOCUMENTS

| EP | 0 080 179 A1 | 6/1983 |
|---|---|---|
| EP | 1 634 554 A2 | 3/2006 |
| WO | WO 2006/005349 A2 | 1/2006 |
| WO | WO 2012/134804 A1 | 10/2012 |
| WO | WO 2013/029622 A1 | 3/2013 |

OTHER PUBLICATIONS

International Search Report, for International Application No. PCT/US2013/031703, dated Jun. 13, 2013.
Written Opinion of the International Searching Authority for International Application No. PCT/US2013/031703, dated Jun. 13, 2013.

*Primary Examiner* — Tatyana Zalukaeva
*Assistant Examiner* — Kai Weng
(74) *Attorney, Agent, or Firm* — Cook Alex Ltd.

(57) ABSTRACT

Catheter assemblies for draining urine from the urinary system of the user are disclosed herein. The catheter assemblies include an outer sleeve that houses the catheter tube and a deployable flexible container. The container is deployable through a slot in the sleeve wall and can be retracted back into the sleeve after use.

20 Claims, 5 Drawing Sheets

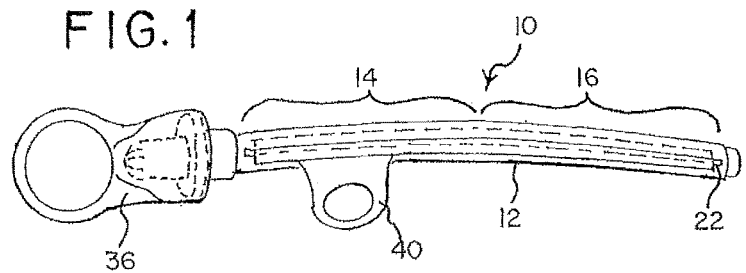
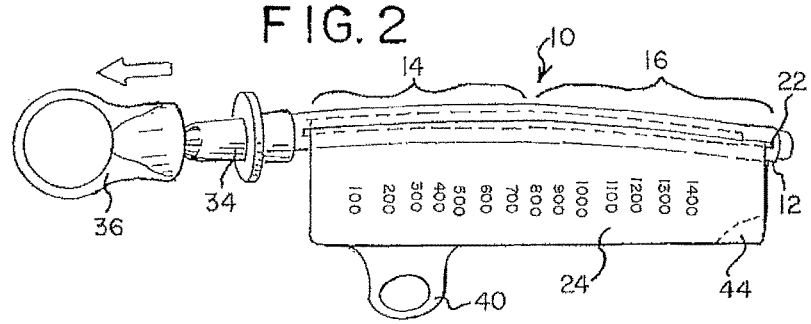
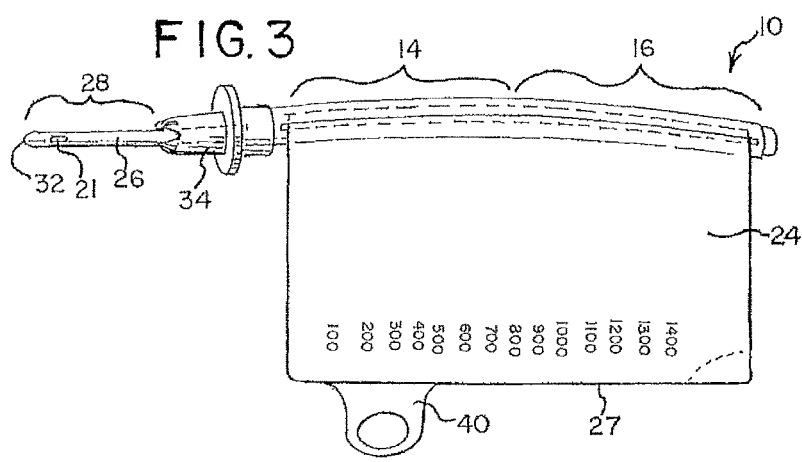

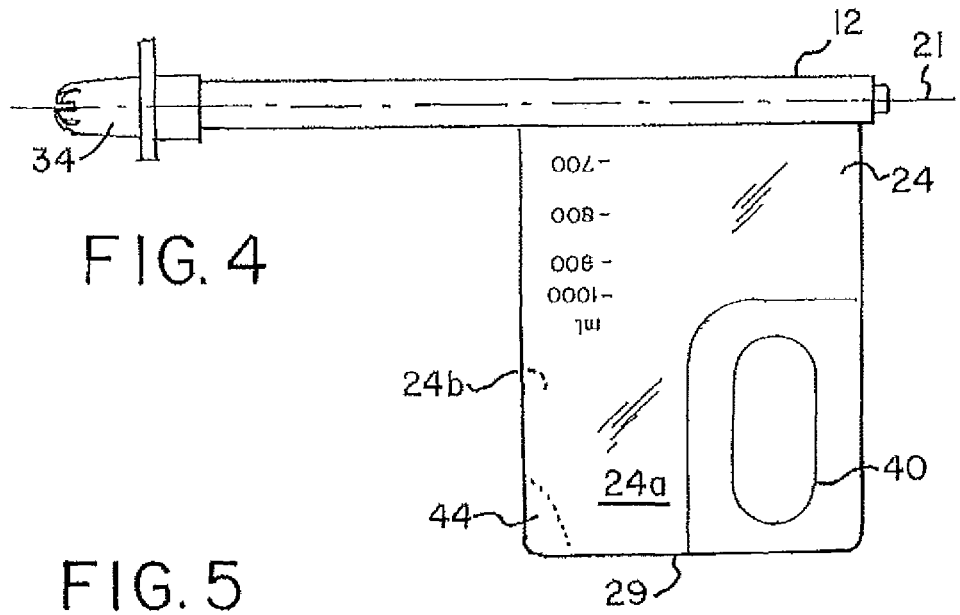
FIG. 4
FIG. 5
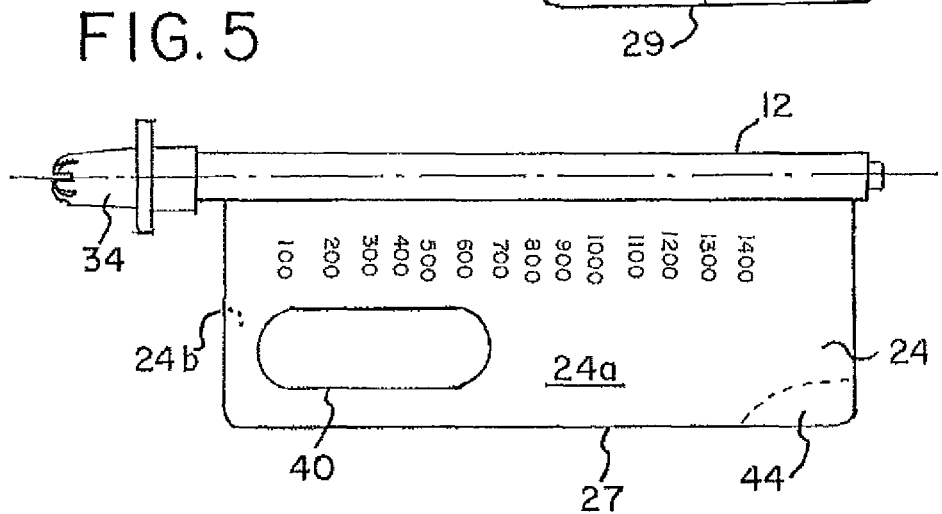
FIG. 6
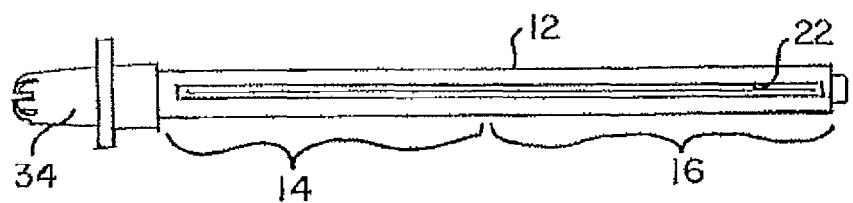

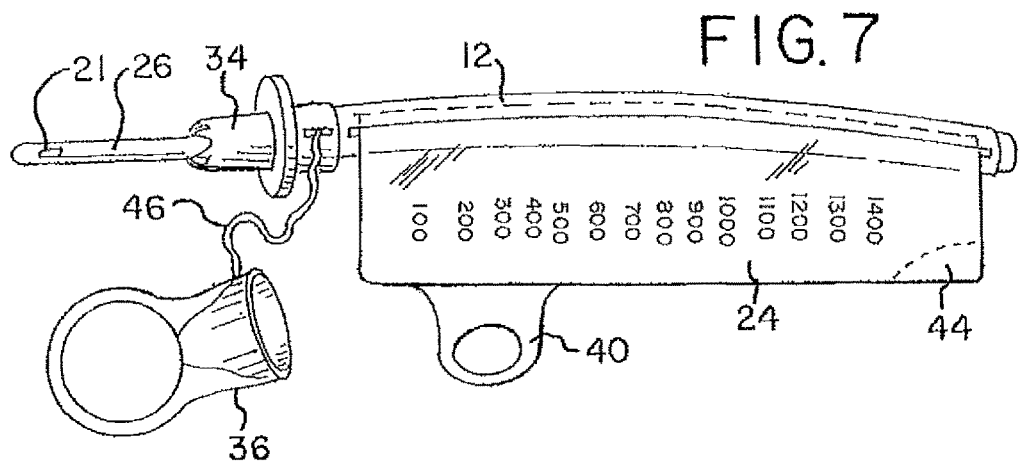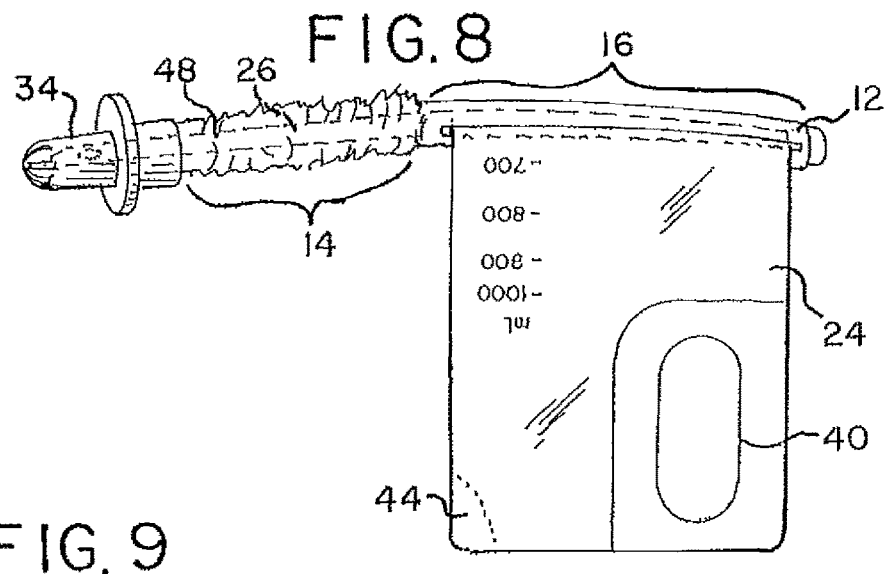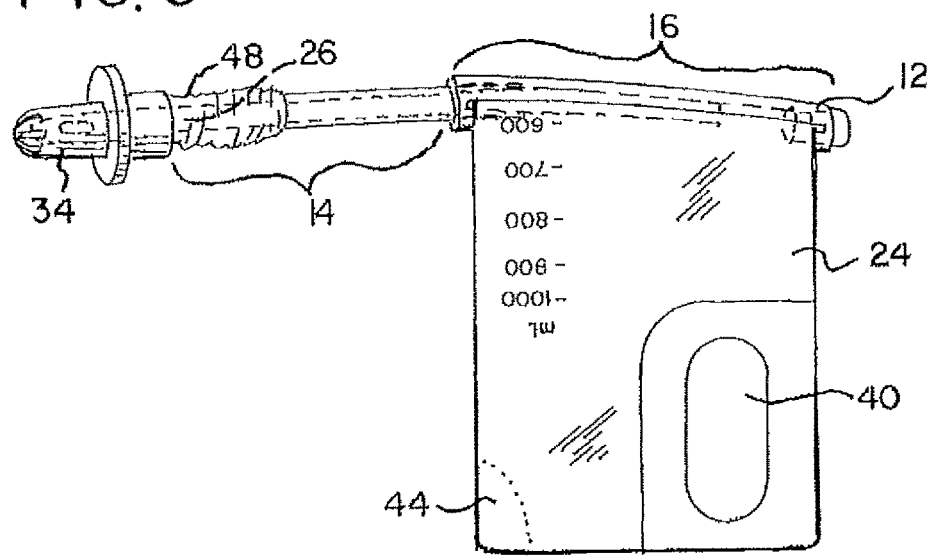

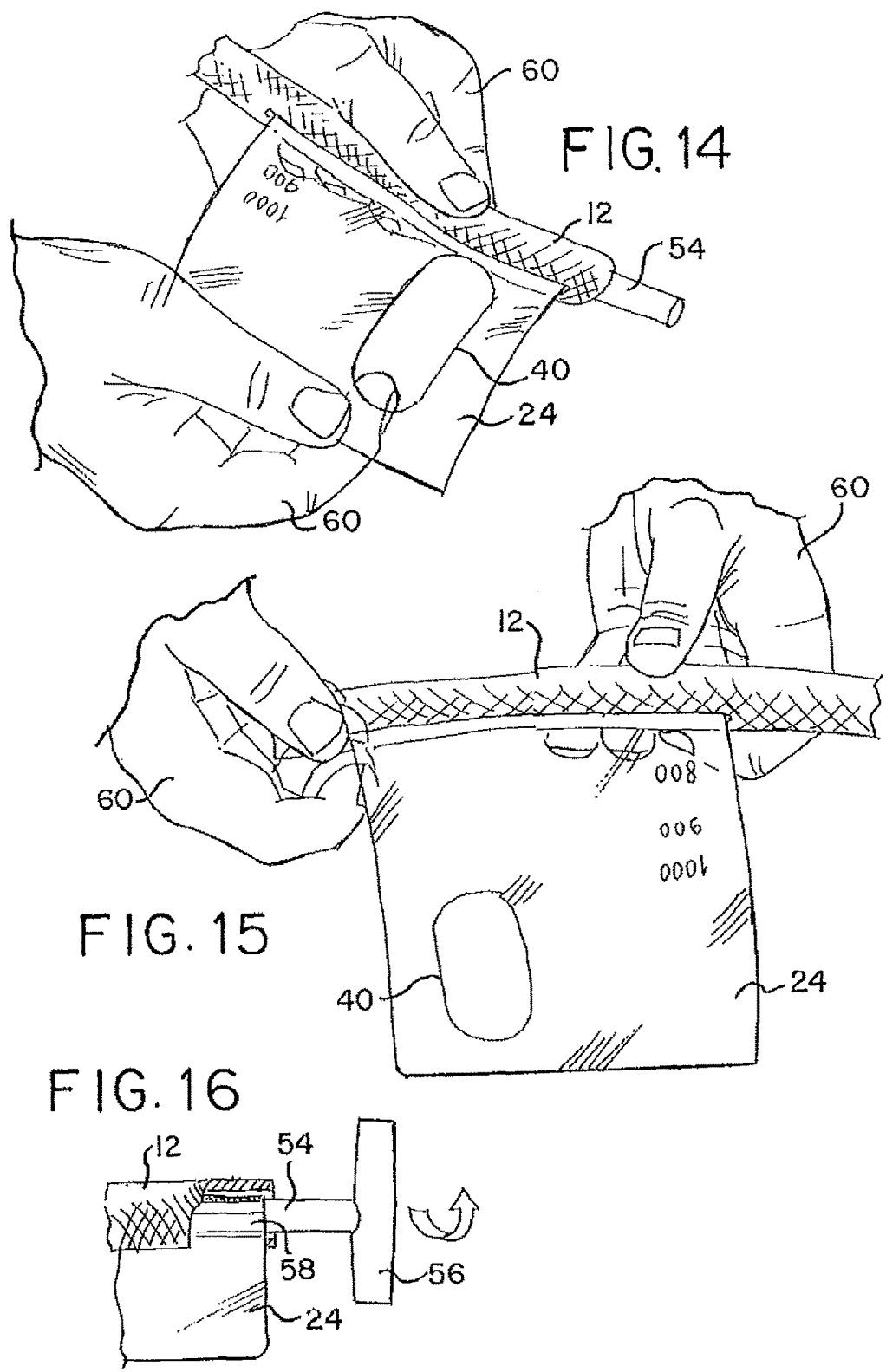

CATHETER ASSEMBLY WITH DEPLOYABLE COLLECTION CONTAINER

The present application is the U.S. National Stage of PCT International Patent Application No. PCT/US2013/031703, filed Mar. 14, 2013, which is incorporated herein by reference.

FIELD OF THE DISCLOSURE

The present disclosure is directed to catheters for use in the medical field. More particularly, the present disclosure is directed to catheters for use in the management of urinary incontinence. Even more particularly, the present disclosure is directed to urinary catheters that are easily manipulated and provided with a pre-attached urine collection container that can be deployed from and returned to the catheter assembly such that the entire catheter assembly can be disposed of in a discreet manner.

BACKGROUND

Catheters are used to treat many different types of medical conditions and typically include an elongated catheter tube that is inserted into and through a passageway or lumen of the body. Urinary catheters and, in particular, intermittent urinary catheters are commonly used by individuals who suffer from certain abnormalities of the urinary system, such as urinary incontinence. With the advent of intermittent urinary catheters, individuals with problems associated with the urinary system can conveniently self-catheterize to drain the individual's bladder. Individuals who suffer from urinary incontinence will often self-catheterize several times a day.

Self-catheterization involves removing the catheter assembly from its package and inserting and advancing the catheter tube through the user's urethra. Often, urinary catheter assemblies include a urine collection container that must either be attached by the user or is pre-attached to the catheter. In many cases, users of intermittent urinary catheters have limited or diminished dexterity that is often the result of spinal cord injuries. Also, users of intermittent catheters are often required to self-catheterize outside the privacy of the home, such as in public restrooms. Thus, for these and other reasons, it is desirable that the intermittent catheters and the urine collection containers associated with catheter assemblies be easy to manipulate and deploy. It is also desirable that the container be discreetly provided and that the entire catheter assembly be disposable in a discreet manner.

BRIEF DESCRIPTION OF THE DRAWINGS

FIG. 1 is a perspective view of one embodiment of the catheter assembly of the present disclosure;

FIG. 2 is a perspective view of the catheter assembly of FIG. 1 with the protective cap being removed and the container being deployed;

FIG. 3 is a perspective view of the catheter assembly of FIGS. 1 and 2 above with the catheter tube being deployed and the container in a deployed condition;

FIG. 4 is a top view of another embodiment of the catheter assembly of the present disclosure;

FIG. 5 is a top view of a further embodiment of the catheter assembly of the present disclosure;

FIG. 6 is a side view of the catheter assembly of, for example, FIG. 5 with the elongated slot in the sleeve wall;

FIG. 7 is a perspective view of an embodiment of the catheter assembly of the present disclosure with a drawstring for deploying the catheter tube;

FIG. 8 is a perspective view of an embodiment of the catheter assembly of the present disclosure with a container housed within the sleeve and the sleeve having a flexible sleeve portion;

FIG. 9 is a perspective view of another embodiment of the catheter assembly of the present disclosure wherein the sleeve includes a sleeve portion having a first diameter, a sleeve portion having a second diameter and a flexible sleeve portion;

FIG. 14 illustrates a step in the deployment of the container from the sleeve of the catheter assembly of the present disclosure;

FIG. 15 illustrates a step in the rewinding of the container into the sleeve of the catheter assembly of the present disclosure; and FIG. 16 is a partial end view of the distal end portion of the spool sub-assembly showing an outer wall of the container attached thereto.

SUMMARY

Figure 10:
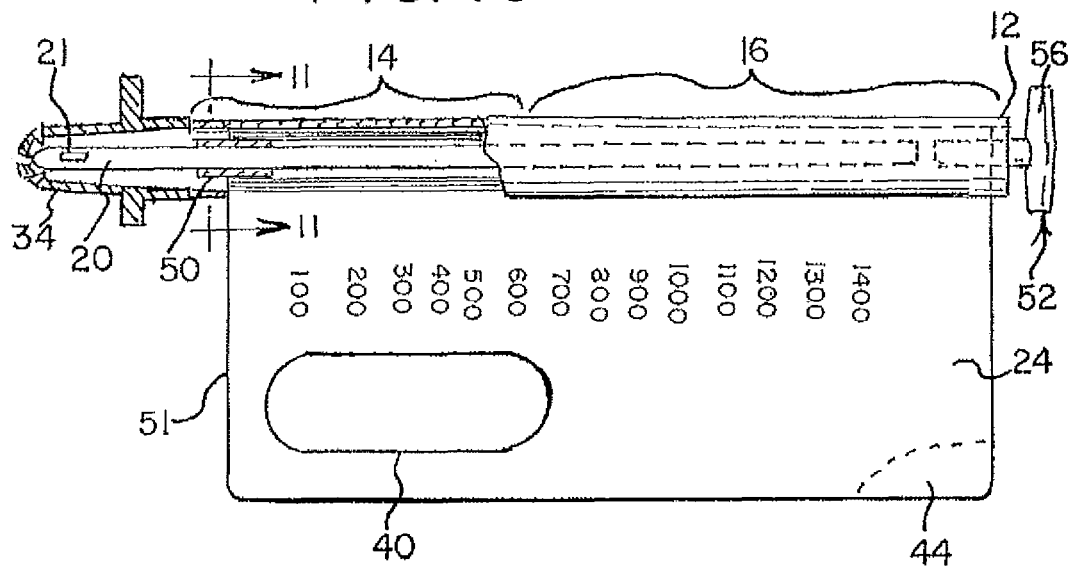
FIG. 10 is a top view of an embodiment of the catheter assembly of the present disclosure with a portion of the sleeve broken-away to show the port communicating with the container and catheter tube and a spool sub-assembly.

In one aspect the present disclosure is directed to a catheter assembly including an elongated sleeve and a flexible container housed within the sleeve. The elongated sleeve has a proximal end portion, a distal end portion and a wall defining an interior compartment between the proximal and distal end portion. The sleeve wall includes an elongated slot. The flexible container housed within the sleeve may be deployable through the slot in the sleeve wall. The catheter assembly of the present disclosure also includes a deployable catheter tube within the sleeve. The catheter tube has a proximal end portion terminating in a closed proximal end tip and an open distal end in flow communication with the container.

In a more specific aspect, the catheter assemblies disclosed herein may include a sleeve, at least a portion of which is rigid. Also, in a more specific embodiment at least a portion of the sleeve may be flexible.

In another more specific aspect, the catheter assemblies disclosed herein may include a distal end sleeve portion having a first diameter and a proximal end sleeve portion having a second diameter. The proximal and distal end portions of different diameters may be provided as separate parts attached to each other to define the full sleeve.

In another more specific aspect, the catheter assemblies disclosed herein may include a spool sub-assembly associated with the catheter assembly for at least retracting and returning the container to the sleeve through the slot in the sleeve wall.

In a further more specific aspect, the catheter assemblies disclosed herein may include a port, one end of which is in flow communication with the catheter tube and the other end of which is in flow communication with the interior of the container.

In another more specific aspect, the catheter assemblies disclosed herein may include an introducer tip at the proximal end tip of the catheter tube.

In yet another specific aspect, catheter assemblies disclosed herein may include a flexible sleeve in the proximal end portion of the sleeve, the flexible sleeve being sufficiently flexible to allow for manipulation of the sleeve by the user.

DESCRIPTION OF THE ILLUSTRATED EMBODIMENTS

The embodiments disclosed herein are for the purpose of providing a description of the present subject matter. The catheter assemblies, methods of use and methods of manufacture disclosed herein may be embodied in various other forms and combinations not specifically described or illustrated. Therefore, specific embodiments are not to be interpreted as limiting, and the features disclosed and illustrated are not to be interpreted as limited to any one specific embodiment as described or illustrated.

FIG. 1 shows an embodiment of the catheter assembly 10 of the present disclosure. Catheter assembly 10 includes an elongated sleeve 12 having a proximal end portion 14 and a distal end portion 16. Sleeve 12 includes an outer wall between proximal end portion 14 and distal end portion 16 that defines an interior compartment 20. As shown in FIGS. 1-3, sleeve 12 includes slot 22 in its outer wall. As further seen in FIGS. 1-3, slot 22 is preferably a narrow opening through which container 24 may be deployed (and retracted).

Catheter assembly 10 further includes deployable catheter tube 26 housed within sleeve 12. Catheter tube 26 likewise has a proximal end portion 28 terminating in a proximal end tip 32, and an open distal end portion 30 that is in flow communication with the interior chamber of container 24. As further shown in FIGS. 1-3, catheter assembly 10 of the present disclosure may preferably include introducer tip 34 which aids in the positioning and protection of catheter proximal end tip 32 during catheterization. Introducer tip 34 is attached to catheter tube 26 at the proximal end tip 32 (e.g., to protect the proximal end tip 32 during insertion into the urethra from bacteria residing in the distal urethra) and includes a plurality of slits in its proximal tip to allow for deployment of catheter tube 26 as shown in FIG. 3. Introducer tip 34 may also include a reservoir that contains a gel or other friction-reducing material which coats catheter tube 26 as it is advanced out from sleeve 12 and into the urethra. Introducer tip 34 may be covered by cap 36 until catheter assembly 10 is ready for use.

Figure 11:
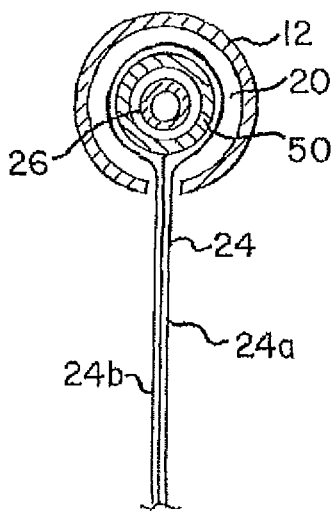
FIG. 11 is a cross-sectional end view of the container and port taken along line 11-11 of FIG. 10.
Figure 13:
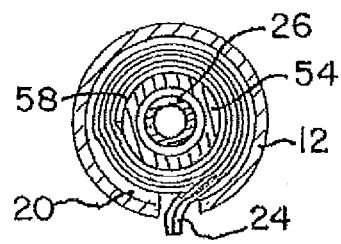
FIG. 13 is a cross-sectional end view of the distal end portion of the catheter assembly including the spool sub-assembly taken along line 13-13 of FIG. 12.
Figure 12:
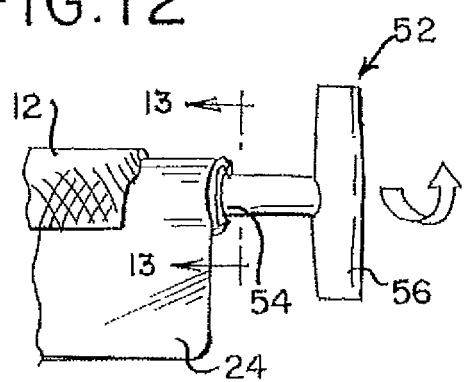
FIG. 12 is an enlarged, partial view of the distal end portion of a catheter assembly of the present disclosure including a container rolled onto the spool of a spool sub-assembly.

As shown in FIGS. 1-3, catheter assembly 10 according to one aspect of the present disclosure includes deployable container 24, which is likewise housed within sleeve 12 until it is ready for use. Container 24 is preferably made of a polymeric material that is sufficiently flexible such that it can be rolled up or otherwise collected within interior compartment 20 of sleeve 12 (FIGS. 11-13). Materials that are suitable for use as container 24 include plasticized polyvinyl chloride (PVC) or other flexible materials that will be known to those of skill in the art.

As shown in FIG. 4, container 24 may be laterally deployed from sleeve 12 relative to the central longitudinal axis 21. Container 24 may be deployed by, for example, being unrolled or unwound from sleeve 12 through slot 22. As container 24 is unrolled, the leading edge of container 24 may be the shorter peripheral edge 29 of container 24. Alternatively the leading edge may be the longer peripheral edge 27 of container 24 as shown in FIG. 5. Container 24 may include printing on the outside of the container wall, such as graduated volume indicators and/or instructions for use. As further shown in FIGS. 1-5, container 24 may include grasping member 40 used to grasp container 24 and deploy it to its ready to use configuration. In one embodiment, grasping member 40 may be a finger hole formed across the walls 24a and 24b of container 24, as shown in FIGS. 4-5. Alternatively grasping member 40 may be a separately attached member such as finger ring or pull tab (40) shown in FIGS. 1-3. In addition, container 24 may include one or more perforations in the container walls that define tear-away tab 44. Tear-away tab 44 may be of any shape and may be located at or near the peripheral edge of container 24. Tear-away tab 44 allows for emptying of container 24 after urine collection has been completed (as described in greater detail below).

With reference to FIG. 6, depending on the orientation and shape of container 24, longitudinal slot 22 may extend along the entire length of sleeve 12 as shown in FIG. 6, or along only a portion of sleeve 12 such as the distal end portion 16 of sleeve 12.

In the catheter assemblies disclosed and described herein, sleeve 12 may be provided as a cylindrical tube of substantially uniform diameter and uniform flexibility/rigidity (as shown, for example, in FIGS. 1-3 and 7). Alternatively, sleeve 12 may be provided as a substantially or partially cylindrical housing of uniform or varying diameter and/or uniform or varying flexibility and rigidity as shown in FIGS. 8 and 9 and described in more detail below. In one embodiment, sleeve 12 may be at least partially made of a rigid polymeric material. For example, sleeve 12 or at least the rigid portion of sleeve 12 may be molded or extruded as a cylindrical tube made of plasticized polyvinyl chloride, polyethylene, polypropylene, or other suitable, biocompatible polymeric materials. Alternatively, sleeve 12 may be constructed of a braided or mesh material such as nylon to provide the rigid sleeve wall. Sleeve 12 protects catheter tube 26 from direct user contact with catheter tube 26. A rigid or partially rigid sleeve 12 also provides added stiffness to catheter assembly 10, which aids during insertion of catheter tube 26 into the urinary canal of the user.

FIG. 8 shows an embodiment of catheter assembly 10 and more particularly of sleeve 12. In the embodiment of FIG. 8, catheter sleeve 12 has distal and proximal end portions 16 and 14, respectively, having a having different degrees of flexibility. In one embodiment, distal end portion 16, which houses container 24, may be made of a substantially rigid polymeric or plastic material of the type identified above. At least a portion of proximal end portion 14 may be flexible, defining a flexible sleeve portion 48. In one embodiment, flexible sleeve portion 48 may be a less rigid, more flexible section of a continuous cylindrical housing that defines interior compartment 20. Alternatively, and as shown in FIG. 8, flexible sleeve portion 48 may be provided as a sheet of flexible material that is attached to the walls of a rigid sleeve portion of sleeve 12. In one embodiment, flexible sleeve portion 48 may be attached to rigid walls of sleeve 12 at one end and to introducer tip 34 at an opposite end. Examples of flexible materials that are suitable for use in providing flexible sleeve portion 48 include thin polymeric materials that can be easily folded or bunched by the user as catheter tube 26 is advanced into the urethra. Thus, flexible sleeve portion 48 may be formed of any one or more of thin, flexible polymeric materials, such as polyethylene, plasticized PVC, polypropylene, polyurethane, or an elastomeric hydrogels. In addition, where hydration of catheter tube 26 is desired, flexible sleeve portion is preferably made of a material that is liquid impermeable and vapor permeable.

As seen in FIG. 8, sleeve 12 (or at least rigid portion of sleeve 12) may preferably be provided as a cylindrical, rigid tube of uniform diameter with flexible sleeve portion 48 associated with the rigid wall at or near proximal end portion 14. The inner diameter of the rigid portion of sleeve 12 should be large enough to accommodate container 24 in its rolled up configuration.

In a further embodiment shown in FIG. 9, sleeve 12 may include a portion (e.g., distal) that has a first diameter sufficient to house container 24 in its rolled up configuration. A second portion of sleeve 12 may be provided as a rigid cylindrical member having a second diameter that is typically smaller than the first diameter of sleeve 12 but sufficient to house catheter tube 26. The portion of sleeve 12 having a smaller diameter is typically proximal to the distal end portion of sleeve 12. As shown in FIG. 9, proximal end portion of sleeve 12 with its smaller diameter may further include flexible sleeve portion 48 of the type described above. The rigid portions of sleeve 12 having different diameters may be provided as separate parts which are then joined to each other such that the lumens of the respective rigid sleeve portions communicate with each other. Catheter tube 26 is housed within and extends through both rigid cylindrical portions and flexible sleeve portion.

In one embodiment, as shown in FIG. 7, catheter tube 26 may be advanced by drawstring 46 which is attached at one end to cap 36 and attached at its other end to catheter tube 26. Pulling on finger ring of cap 36 advances catheter tube 26 as described, for example, in U.S. Provisional Patent Application No. 61/636,218, filed Apr. 20, 2012, which is incorporated herein by reference in its entirety. Where sleeve 12 includes a flexible sleeve portion 12 as shown in FIGS. 8-9, catheter tube 26 may be manually advanced by grasping catheter tube 26 through the no-touch flexible sleeve portion 48 and sliding tube 26 forward.

Catheter tube 26 is typically made of a flexible, biocompatible polymeric material. Suitable polymers include polyvinyl pyrrolidone (PVP), as well as other materials such as polyamide, polyanhydride, polyether, poly(ether imide), poly(ester imide), polyvinyl alcohol, polyvinyl chloride, polycarbonate, poly(ε-caprolactone) with polymethylvinylsiloxane, poly(ethylene-co-(vinylacetate)) with dicumylperoxide, poly(D-lactide), poly(L-lactide), poly(DL-lactide) and poly(glycolide-co-(ε-caprolactone))-segments, multiblock copolyesters from poly(ε-caprolactone) and PEG and chain extender based on cinnamic acid groups, poly(ε-caprolactone) dimethacrylate and n-butyl acrylate, oligo(ε-caprolactone) diols, oligo (p-dioxanone) diols and diisocyanate, linear density polyethylene, linear low density polyethylene, high density polyethylene, polypropylene. Catheter tube 26 is made of a biocompatible polymeric material that has sufficient flexibility to allow for movement and advancement through the urethra of a user, but not so stiff that it would make movement and advancement of tube 26 through the urethra difficult or painful. Catheter tube 26 may have a length suited for the intended user. For example, catheters for male users typically have a length of between 30 cm and 40 cm. Catheters for female users are quite shorter and typically have a length of between 100 and 120 mm.

Catheter tube 26 may also be made of a hydrophilic material. Catheter tube 26 may alternatively or additionally include a hydrophilic coating on at least a portion of the outer surface thereof, which when contacted by an aqueous or other liquid provides or enhances lubricity (and reduces the coefficient of friction) of catheter tube 26. Catheter tubes that are activated by agents to make the catheter tube 26 more lubricious are known and are sold in products under the trademarks VaPro™ and VaPro™ Plus, distributed by Hollister Inc. of Libertyville, Ill. Additional details of such hydrophilic catheters and the activation thereof are described in U.S. Pat. No. 8,051,981, which is incorporated herein by reference. Alternatively, as discussed above, catheter tube 26 may be lubricated by providing a friction-reducing material such as a gel within a reservoir of introducer tip 34, which coats catheter tube 26 as catheter tube passes through introducer tip 34. Catheter assemblies that include a gel reservoir in a protective introducer tip are sold in products under the names Advance™ and Advancer™ Plus, also distributed by Hollister Inc. of Libertyville, Ill. Catheter tube 26 includes a plurality of eyelet openings 21 through which urine enters the flow path of catheter tube 26.

As shown in FIG. 10, catheter assemblies of the present disclosure preferably include a port 50 within sleeve 12. Port 50 includes open proximal and distal ends and is attached to container 24 to establish flow communication with interior chamber of container 24. Port 50 is preferably attached to container 24 along proximal edge 51 of container 24. As shown in FIG. 11, opposed walls 24a and 24b of container 24 are attached to outer wall of port 50 by, for example, heat sealing or the like. Interior channel of port 50 is sized to allow for free movement of catheter tube 26 through port 50 during use. Thus, sleeve 12, port 50 and catheter tube 26 are concentrically disposed relative to each other, as shown in FIG. 11. Where a further rigid sleeve member 12 that is proximal to distal end portion 16 (as shown, for example, in FIG. 9) is provided, the portion of sleeve 12 having a larger diameter, the portion of sleeve 12 having a smaller diameter, port 50 and catheter tube 26 are all concentrically disposed relative to each other. Catheter tube 26 may include a flared end or a stopper formed or placed at or near its distal end to prevent catheter tube 26 from being advanced too far out of port 50. In one embodiment, the stopper may be made of the same material as catheter tube 26, as described below.

As also shown in FIG. 10 and further shown in FIGS. 12-13, catheter assembly may include spool sub-assembly 52 for rewinding container 24 at the distal end of catheter assembly 10. In one embodiment, spool sub-assembly 52 may include a spool member 54 to which container 24 is attached and onto which container 24 is rolled in its initial configuration before deployment and after container has been emptied. FIGS. 12-13 show container 24 in its wound up configuration over and about spool member 54. In one embodiment, a portion of outer wall 58 of container 24 may be attached to the outer surface of spool 54, as shown in the end view of FIG. 13 and in FIG. 16. Spool member may have a length sufficient to collect (e.g., roll) container 24 evenly within sleeve compartment 20. Rotation of spool member 54 is achieved by turning rotatable knob or handle 56 of spool sub-assembly, as shown in FIG. 12.

FIGS. 14-15 illustrate steps in the method of deploying and rewinding container 24 from the catheter assembly 10 of the present disclosure. As shown in FIG. 14, user 60 grasps container 24 at grasping member 40 (finger hole, finger ring or pull tab, etc.) and pulls container 24 away from sleeve 12 through slot 22. In a preferred embodiment, grasping member 40 is provided at least partially disposed outside of sleeve 12 to allow for initial grasping. Once deployed, the user 60 may remove protective cap 36 from introducer tip 34. Introducer tip 34 may then be aligned with the opening to the urinary canal, i.e., urethral opening, and inserted into the distal urethra. Catheter tube 26 may then be advanced in the manner described above, such as by drawstring 46 or by manual manipulation and advancement of catheter tube 26 through flexible sleeve portion 48. Once urine begins to flow, it is collected in the now deployed container 24. Once the urine has been collected, it may be emptied from container 24 by tearing tab 44 and emptying the urine into an appropriate permanent container (toilet, WC). Container 24 may then be manually retracted/rewound back into sleeve 12 as shown in FIG. 15 and described above, and the entire used catheter assembly 10 may be disposed of in a waste container.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. A catheter assembly comprising:
   a) an elongated sleeve having a proximal end portion, a distal end portion and a wall defining an interior compartment between said proximal and distal ends, said wall including an elongated slot communicating with said compartment;
   b) a flexible container housed within said sleeve and deployable through said slot in said wall; and
   c) a deployable catheter tube housed within said sleeve, said catheter tube having a proximal end terminating in a closed proximal tip and an open distal end in flow communication with said container.

2. The catheter assembly of claim 1 further comprising a port in flow communication with said container and said catheter tube.

3. The catheter assembly of claim 1 wherein at least a portion of said sleeve wall is rigid.

4. The catheter assembly of claim 1 wherein at least a portion of said sleeve is flexible.

5. The catheter assembly of claim 4 wherein said sleeve is flexible at said proximal portion.

6. The catheter assembly of claim 4 wherein at least said portion of said sleeve is sufficiently flexible to allow for manipulation of said catheter tube by the user.

7. The catheter assembly of claim 1 further comprising an introducer tip.

8. The catheter assembly of claim 7 wherein said introducer tip is attached to the proximal end portion of said sleeve.

9. The catheter assembly of claim 1 wherein said sleeve comprises a distal portion sleeve having a first diameter and a proximal sleeve having a second diameter.

10. The catheter of claim 9 wherein said slot in said wall is in said distal end portion and said container is housed within said distal end portion.

11. The catheter of claim 9 wherein said proximal sleeve portion includes a flexible sleeve portion.

12. The catheter assembly of claim 11 wherein at least said flexible sleeve portion is sufficiently flexible to allow for manipulation of said catheter tube by the user.

13. The catheter assembly of claim 1 further comprising a spool sub-assembly associated with said container for at least returning said container to said sleeve through said slot.

14. The catheter assembly of claim 13 wherein said spool sub-assembly is at said distal end portion of said sleeve.

15. The catheter assembly of claim 13 wherein said spool sub-assembly comprises a spool member about which said container can be wound.

16. The catheter assembly of claim 15 wherein said spool member is attached to an outer wall surface of said container.

17. The catheter assembly of claim 1 further comprising a drawstring attached to said catheter tube.

18. The catheter assembly of claim 1 wherein said container comprises a perforation that defines a detachable portion of said container.

19. The catheter assembly of claim 1 wherein said container comprises a grasping member.

20. The catheter assembly of claim 19 wherein said grasping member comprises a pull ring.

* * * * *